United States Patent
Nicot et al.

(10) Patent No.: US 9,423,365 B2
(45) Date of Patent: Aug. 23, 2016

(54) T2-CUTOFF DETERMINATION USING MAGNETIC SUSCEPTIBILITY MEASUREMENTS

(75) Inventors: Benjamin Nicot, Rio de Janeiro (BR); Patrice Ligneul, Al-Khobar (SA); Mamood Akbar, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1060 days.

(21) Appl. No.: 13/439,183

(22) Filed: Apr. 4, 2012

(65) Prior Publication Data

US 2013/0265043 A1    Oct. 10, 2013

(51) Int. Cl.
    G01V 3/32     (2006.01)
    G01N 24/08    (2006.01)

(52) U.S. Cl.
    CPC .............. *G01N 24/081* (2013.01); *G01V 3/32* (2013.01)

(58) Field of Classification Search
    USPC .......................... 324/300–322; 600/407–435; 382/128–131
    See application file for complete search history.

(56) References Cited

U.S. PATENT DOCUMENTS

| | | | | |
|---|---|---|---|---|
| 2,984,781 A * | 5/1961 | Schwede | | 324/301 |
| 3,135,912 A * | 6/1964 | Baker et al. | | 324/303 |
| 4,933,638 A * | 6/1990 | Kleinberg et al. | | 324/303 |
| 5,387,865 A * | 2/1995 | Jerosch-Herold et al. | | 324/303 |
| 5,629,623 A | 5/1997 | Sezginer et al. | | |
| 6,115,671 A | 9/2000 | Fordham | | |
| 6,833,699 B2 * | 12/2004 | Galford et al. | | 324/303 |
| 6,859,034 B2 * | 2/2005 | Chen | | 324/303 |
| 7,221,158 B1 * | 5/2007 | Ramakrishnan | | 324/303 |
| 7,439,743 B2 | 10/2008 | Potter | | |
| 7,675,287 B2 * | 3/2010 | Minh | | 324/303 |
| 7,893,692 B2 * | 2/2011 | Minh | | 324/303 |
| 2003/0094946 A1 * | 5/2003 | Galford et al. | | 324/303 |
| 2007/0132451 A1 * | 6/2007 | Ramakrishnan | | 324/303 |
| 2010/0026293 A1 * | 2/2010 | Minh | | 324/303 |
| 2010/0109664 A1 * | 5/2010 | Minh | | 324/303 |
| 2013/0265043 A1 * | 10/2013 | Nicot et al. | | 324/303 |

FOREIGN PATENT DOCUMENTS

EP    0908722 A2    4/1999

OTHER PUBLICATIONS

Foley, I., Farooqui, S. A., and Kleinberg, R. L., "Effect of Paramagnetic Ions on NMR Relaxation of Fluids at Solid Surfaces", Journal of Magnetic Resonance, Series A, Nov. 1996, vol. 123(1); pp. 95-104.

(Continued)

*Primary Examiner* — Melissa Koval
*Assistant Examiner* — Tiffany Fetzner
(74) *Attorney, Agent, or Firm* — Bridget M. Laffey

(57) ABSTRACT

Systems and methods for determining T2 cutoff are described. T2 cutoff can be derived from magnetic susceptibility measurements. By providing a depth curve of T2cutoff, improved permeability estimations from NMR can be generated. By combining a magnetic susceptibility tool and an NMR tool, a dynamic T2cutoff can then be provided, together with the standard NMR log, according to some embodiments. According to some embodiments the improved permeability estimations can be provided automatically and in real time at the wellsite.

20 Claims, 7 Drawing Sheets

(56) References Cited

OTHER PUBLICATIONS

Kleinberg, R. L, and Boyd, A., "Tapered Cutoffs for Magnetic Resonance Bound Water Volume", SPE 38737, SPE Annual Technical Conference and Exhibition, Oct. 1997, vol. Omega(Part 2): pp. 197-202.

Chen, S., Ostroff, G., and Georgi, D. T., "Improving Estimation of NMR Log T2 Cuttoff Value with Core NMR and Capillary Pressure Measurements", SCA 9822, 1998: pp. 1-12.

Korb, J-P, Freiman, G., Nicot, B., and Ligneul, P., "Dynamical Surface Affinity of Diphasic Liquids as a Probe of Wettability of Multimodal Porous Media", Physical Review E80, 2009, vol. 80(6) 061601: pp. 1-12.

Korb, J-P, "Nuclear Magnetic Relaxation of Liquids in Porous Media", New Journal of Physics, Mar. 2011, vol. 13(3): pp. 1-26.

International Search Report and Written Opinion of PCT Application No. PCT/US2012/066974 dated Apr. 3, 2013: pp. 1-16.

\* cited by examiner

Legend:
722 = cylindrical magnet
726 = RF antenna
746 = non-magnetic cover
752 = pressure feed-through
753 = pressure feed-through
756 = transformer

T2-CUTOFF DETERMINATION USING MAGNETIC SUSCEPTIBILITY MEASUREMENTS

BACKGROUND

In the field of evaluation of hydrocarbon-bearing subterranean rock formations, a downhole nuclear magnetic resonance (NMR) tool can be used to measure the nuclear magnetic properties of formation hydrogen. Core and log measurements include T2 decay presented as a distribution of T2 amplitudes versus time at each sample depth, typically from 0.3 ms to 3 s. NMR tool measured T2 distributions can be used to describe the fluids contained in a porous rock. It is useful to distinguish between movable and non-movable fluids. In the T2 scale, this can be done by applying a T2cutoff. If T2<T2cutoff, then the fluid is non-movable, if T2>T2cutoff, then the fluid is movable.

For some time in the oil industry, standard T2cutoff values have been used, such as 33 ms for clastics and 90 ms for carbonates. However, these values are frequently found unrealistic for log interpretation as a result of mineralogy dependent surface relaxivity effects which shift the T2 spectra. A known solution is to calibrate T2cutoff values with using laboratory NMR measurements on core samples.

However, the laboratory determination of T2cutoff using core samples and NMR measurements is a relatively long and expensive process. First, core samples are used, which are obtained from the formation. Second, an experimental procedure may be used that includes: (1) cleaning the sample; (2) 100% saturating the sample with water; (3) making NMR T2 measurements; (4) desaturating the sample by spinning in a centrifuge; and (5) making additional NMR T2 measurements. These NMR measurements are then used to determine the value of the T2cutoff. Furthermore, while a laboratory study can provide the correct values of T2cutoff to be used in log interpretation, it provides only values of T2cutoff at depths at which rock core samples were obtained and tested. Moreover, laboratory studies are generally performed at ambient conditions of temperature and pressure, therefore ignoring any potential effect of these parameters on the NMR response.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method for determining T2 cutoff is described. The method includes: receiving magnetic susceptibility data representing magnetic susceptibility measurements made of a rock medium; determining a value for T2 cutoff based at least in part on the magnetic susceptibility data; receiving T2 distribution data representing NMR measurements; and applying the determined T2 cutoff value to the T2 distribution data. According to some embodiments, the rock medium is a hydrocarbon-bearing subterranean rock formation traversed by at least one wellbore. The measurements can be made, for example using wireline and/or LWD tools.

According to some embodiments, the magnetic susceptibility data and T2 distribution data form depth logs along a depth of the wellbore, and the T2 cutoff values are continuously determined over the depth interval. According to some embodiments, T2 cutoff determination uses a relationship of the form $$T2 \approx \frac{1}{A*\chi + B},$$

where $\chi$ represents magnetic susceptibility and A and B are constants.

According to some embodiments, a system for evaluating a hydrocarbon-bearing subterranean rock formation is described. The system includes: a magnetic susceptibility tool adapted to make magnetic susceptibility measurements of the rock formation from within a borehole; a nuclear magnetic resonance tool adapted to make T2 distribution measurements of the rock formation from within a borehole; and a processing system adapted and programmed to determine a value for T2 cutoff based on measurements from the magnetic susceptibility tool, and to apply the determined T2 cutoff value to T2 distribution data from the nuclear magnetic resonance tool.

According to some embodiments a system for generating values for T2 cutoff over a depth interval of a wellbore traversing a subterranean rock formation is described. The method includes: receiving downhole data representing measurements made at a plurality of depths within the depth interval of the rock formation; determining values for T2 cutoff for each of the plurality of depths within the depth interval, the values being based on the downhole data; receiving T2 distribution data representing NMR measurements made at the plurality of depths within the depth interval; and applying the determined T2 cutoff values to the T2 distribution data to yield permeability data at each of the plurality of depths within the depth interval.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details of the subject disclosure in more detail than is necessary for the fundamental understanding of the subject disclosure, the description taken with the drawings making apparent to those skilled in the art how the several forms of the subject disclosure may be embodied in practice. Further, like reference numbers and designations in the various drawings indicate like elements.

Figure 1:
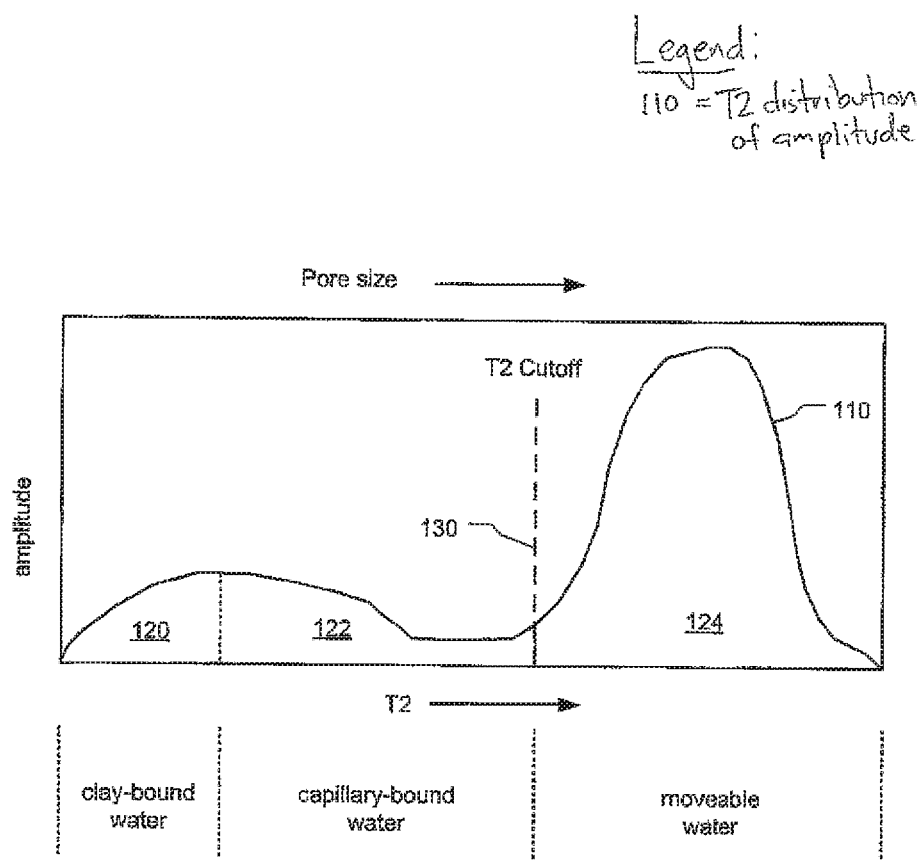
FIG. 1 illustrates an example of T2 distribution interpretation, according to some embodiments.

In the oil Industry, NMR T2 distributions are used to describe the fluids contained in a porous rock. It is useful to distinguish between movable and non-movable fluids. In the T2 scale, this is done by applying a T2cutoff. If T2<T2cutoff, then the fluid is non-movable, if T2>T2cutoff, then the fluid is movable. FIG. 1 illustrates an example of T2 distribution interpretation, according to some embodiments. The T2 distribution of amplitude is plotted in line 110. The T2cutoff 130 is shown and separates the region 124 which represents moveable water, from regions 120 and 122 that represent clay-bound water and capillary-bound water in this example. The T2 distribution 110 can thus be interpreted, and permeability and non-moveable fluids can be extracted from the NMR logs.

According to some embodiments, an approach is based on a general equation describing NMR relaxation processes:

$$\frac{1}{T_2} = \frac{1}{T_{2Bulk}} + \rho_2 \frac{S}{V}$$

Where $T_{2Bulk}$ is the $T_2$ of the fluid outside the rock, $\rho_2$ is the relaxivity of the rock for a given fluid, and S/V is the surface to volume ratio of a given pore, under the assumption of spherical pores, S/V=3/r, where r is the pore radius. If the fluid filling the pores has a long $T_{2Bulk}$, which is the case of water, the bulk term can be neglected and the equation becomes:

$$\frac{1}{T_2} = \rho_2 \frac{3}{r}$$

Therefore, the determination of the value of the smallest pore that has been emptied $r_{cutoff}$ can be performed using NMR to measure the corresponding T2cutoff.

Thus, the value of T2cutoff depends not only on the pore radius $r_{cutoff}$, but also on the relaxivity $\rho_2$ of the rock. Depending on the particular chemistry of a given rock sample, the surface relaxivity changes, therefore causing variations of the T2cutoff values.

In one example, variations in paramagnetic species such as Iron and Manganese with depth can be directly correlated to variations of T2cutoff. According to some embodiments magnetic susceptibility of the rock is measured to estimate the quantity of paramagnetic impurities and therefore estimate a value for T2cutoff. The variations of magnetic susceptibility is directly correlated to the quantity of paramagnetic impurities in the rock by the curie law:

$$\chi_g = \frac{1}{4\pi\rho_{rock(cgs)}} \times \frac{[M]\%\rho_{rock(SI)}N_A}{100 \times MW_M} \times \frac{\mu_0(n_B\mu_B)^2}{3kT}$$

Figure 2:
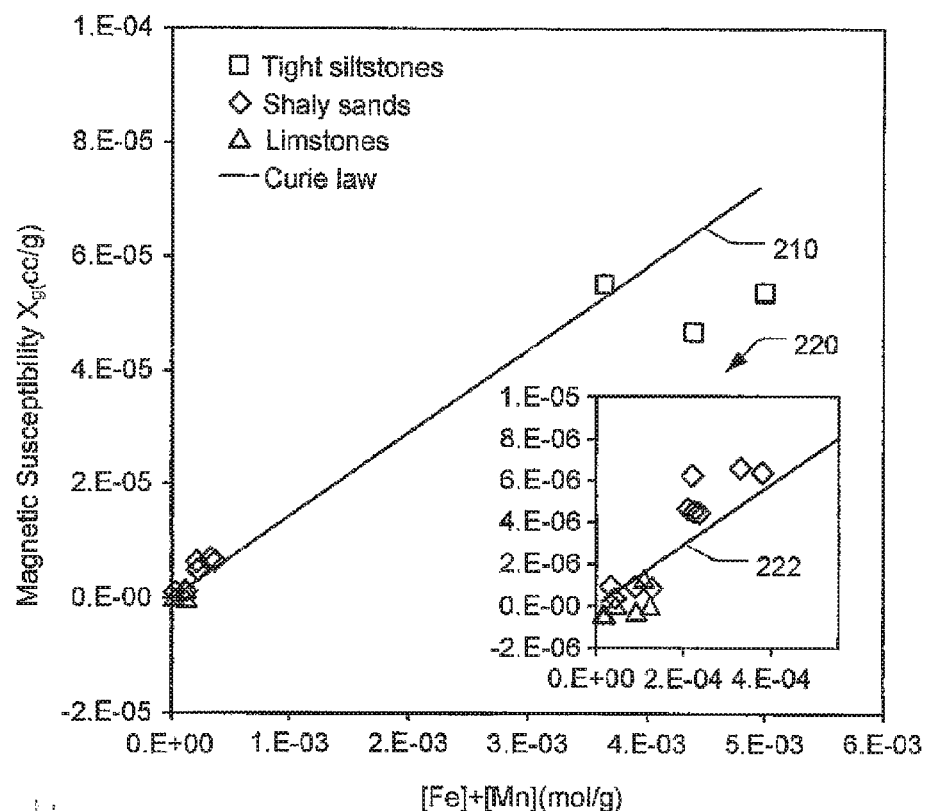
FIG. 2 illustrates an example of a linear relationship between magnetic susceptibility and the quantity of paramagnetic ions.

FIG. 2 illustrates an example of a linear relationship between magnetic susceptibility and the quantity of paramagnetic ions. The quantities of ions were measured by ICPAE (Atomic Emission Inductively Coupled Plasma) and the magnetic susceptibility was measured independently. The curie law is shown in line 210 and in line 222 in the detailed sub-plot 220.

Figure 3:
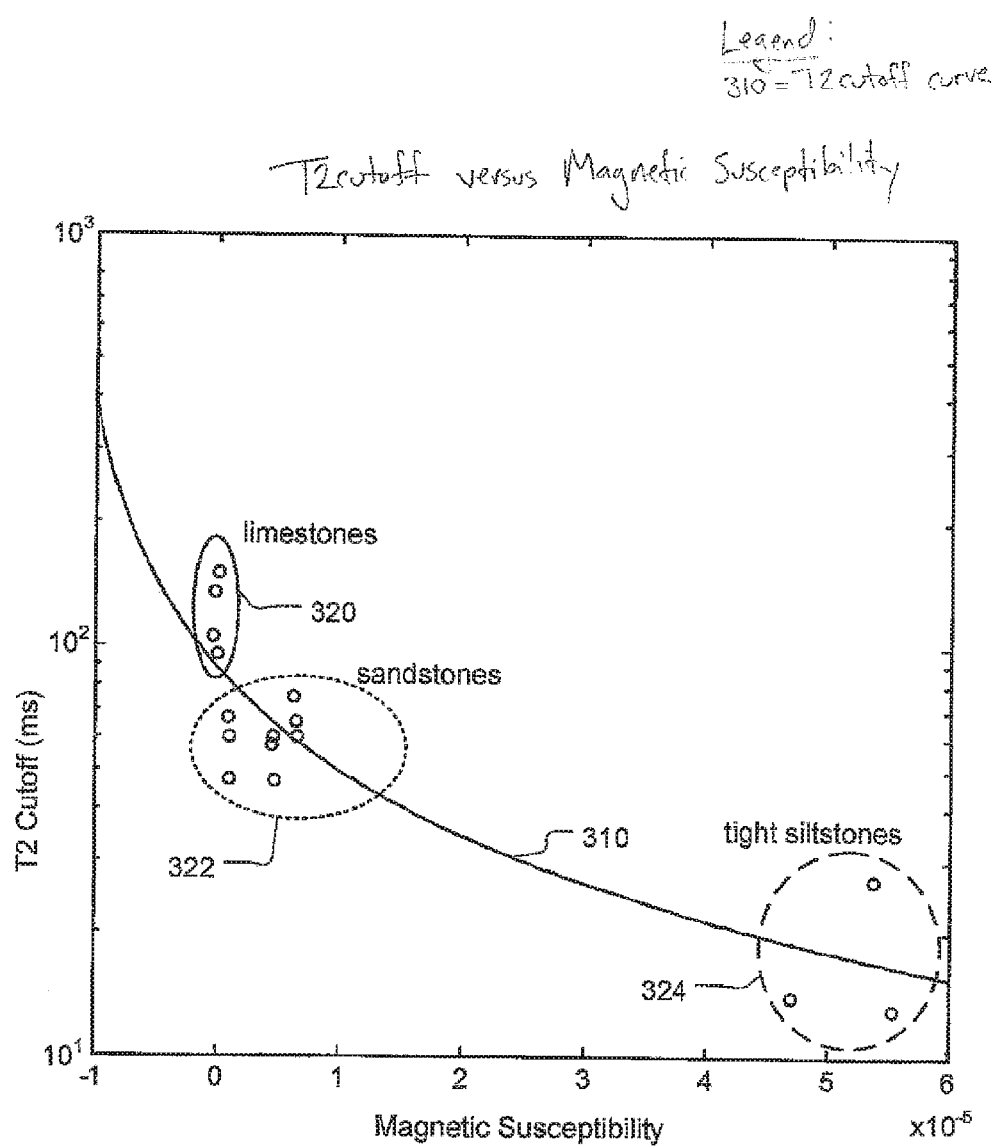
FIG. 3 is a plot of T2cutoff versus magnetic susceptibility for three different types of rock.

FIG. 3 is a plot of T2cutoff versus magnetic susceptibility for three different types of rock. In particular, limestone is shown in group 310, sandstones in group 322 and tight siltstones in group 324. From FIG. 3, it is clear that Magnetic susceptibility can be used as a proxy for determining an estimated value of T2cutoff.

From J-P Korb, G. Freiman, B. Nicot, P. Ligneul, Dynamical surface affinity of diphasic liquids as a probe of wettability of multimodal porous media, Physical Review E 80, 061601, 2009, the expression of T2 (or T1) can be expressed as a function of the paramagnetic content of the rock:

$$\frac{1}{T_2} \approx \frac{1}{T_{2bulk}} + \left[\frac{N_{param}}{N}\right]\frac{1}{T_{2param}}$$

And $N_{param}$ is proportional to the volumetric concentration of paramagnetics present in the sample.

Accordingly, there is a direct relationship between a measured T2 and the magnetic susceptibility of the rock and this relationship is of the form:

$$T_2 \approx \frac{1}{A * \chi + B}$$

As can be seen from FIG. 3, in our study the T2cutoff and magnetic susceptibility correlates well and the points group by rock type. A curve 310 fit using the above equation shows the pertinence of the model. In the case shown in FIG. 3, the fitting parameters obtained are A=880, B=0.0114.

Figure 4:
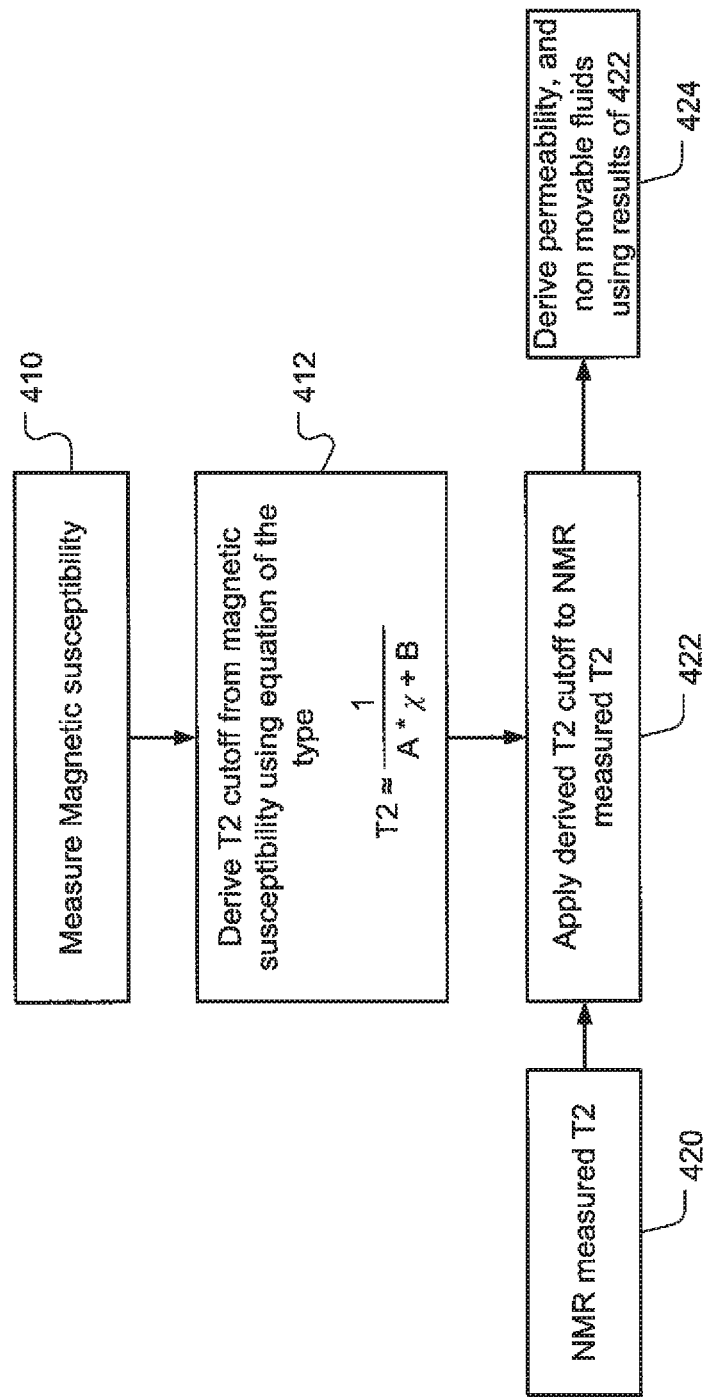
FIG. 4 is a flowchart illustrating a workflow to derive the value of T2cutoff from a measurement of magnetic susceptibility, according to some embodiments.

FIG. 4 is a flowchart illustrating a workflow to derive the value of T2cutoff from a measurement of magnetic susceptibility, according to some embodiments. In block 410 the magnetic susceptibility is measured. In block 412 the T2cutoff is derived using an equation of the type:

$$T_2 \approx \frac{1}{A * \chi + B}.$$

In block 420, T2 is measured, for example using a downhole NMR tool. In block 422 the T2cutoff derived in block 412 is applied to the T2 distribution data. In block 424 the permeability and/or non movable fluids are derived using the applied T2cutoff.

For laboratory applications, the devices to measure magnetic susceptibility are commercially available.

Figure 5:
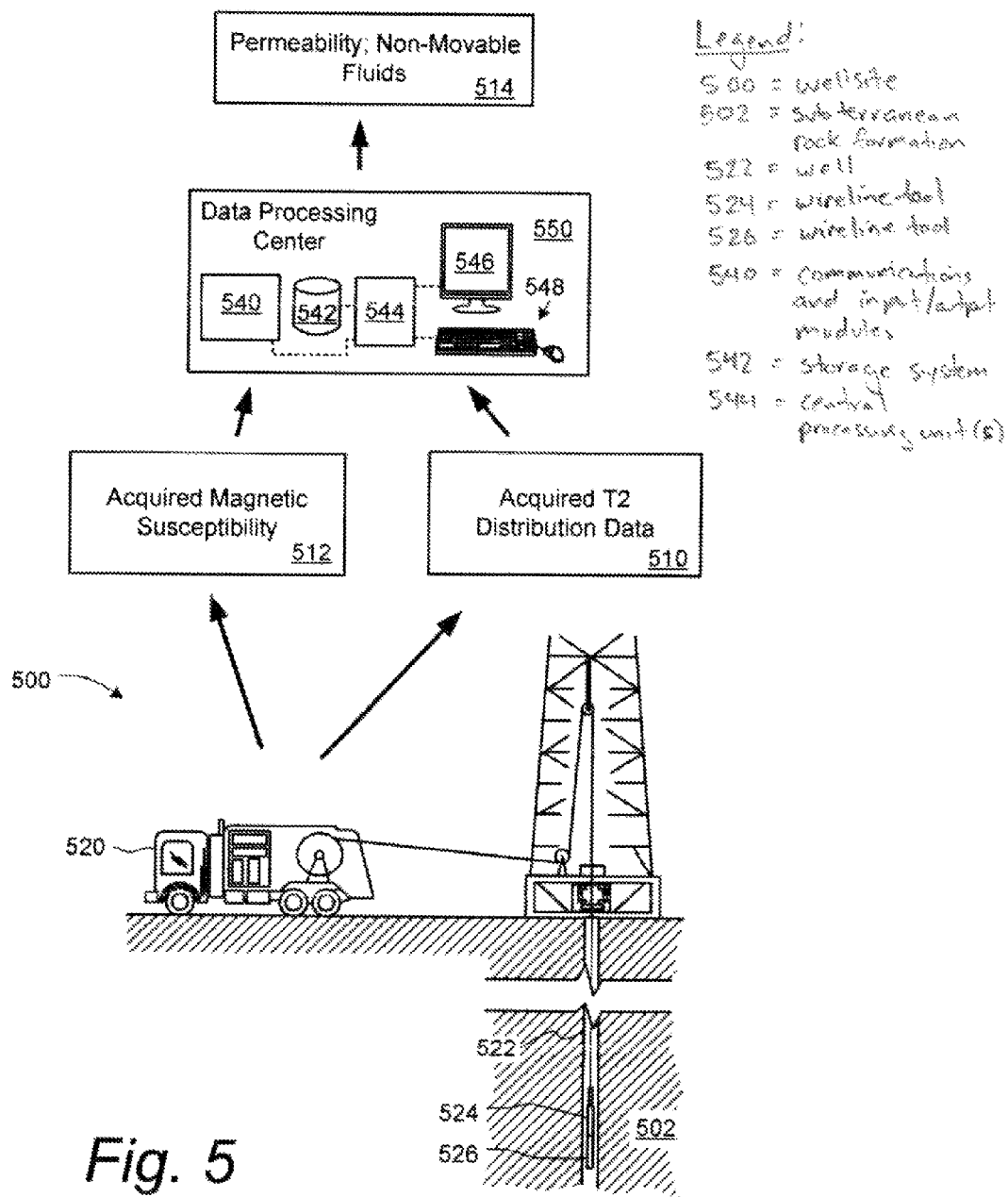
FIG. 5 shows systems to determine T2cutoff using magnetic susceptibility measurements, according to some embodiments.

FIG. 5 shows systems to determine T2cutoff using magnetic susceptibility measurements, according to some embodiments. Data from a subterranean rock formation 502 is being gathered at wellsite 500 via a wireline truck 520 deploying a wireline tool string in well 522. The tool string includes one or more wireline tools such as tools 524 and 526. According to some embodiments, wireline tool 524 is an NMR tool adapted to make NMR measurements downhole, including gathering T2 distribution data. According to some embodiments an NMR tool such as Schlumberger's CMR Combinable Magnetic Resonance Tool is used. According to some embodiments, wireline tool 526 is a downhole tool adapted to measure magnetic susceptibility. In one example a tool such as discussed in U.S. Pat. No. 7,439,743, which is incorporated herein by reference, can be used.

Acquired T2 distribution data 510 and magnetic susceptibility data 512 from tools 524 and 526 respectively are transmitted to a processing center 550 which includes one or more central processing units 544 for carrying out the data processing procedures as described herein, as well as other processing. The processing center includes a storage system 542, communications and input/output modules 540, a user display 546 and a user input system 548. According to some embodiments, the processing center 550 may be located in a location remote from the wellsite 500. Data processing center 550 carries out the T2cutoff determination, such as described in block 412 of FIG. 4. Data processing center 550 also carries out the application of the derived T2cutoff to the T2 distribution data 510 and derives results 514 such as permeability and non-moveable fluid information, such as described in blocks 422 and 424 of FIG. 4. According to some embodiments, the magnetic susceptibility data 512 and the T2 distribution data 510 are acquired at different times in the same well, or in different wells at the same time or at different times.

Figure 6:
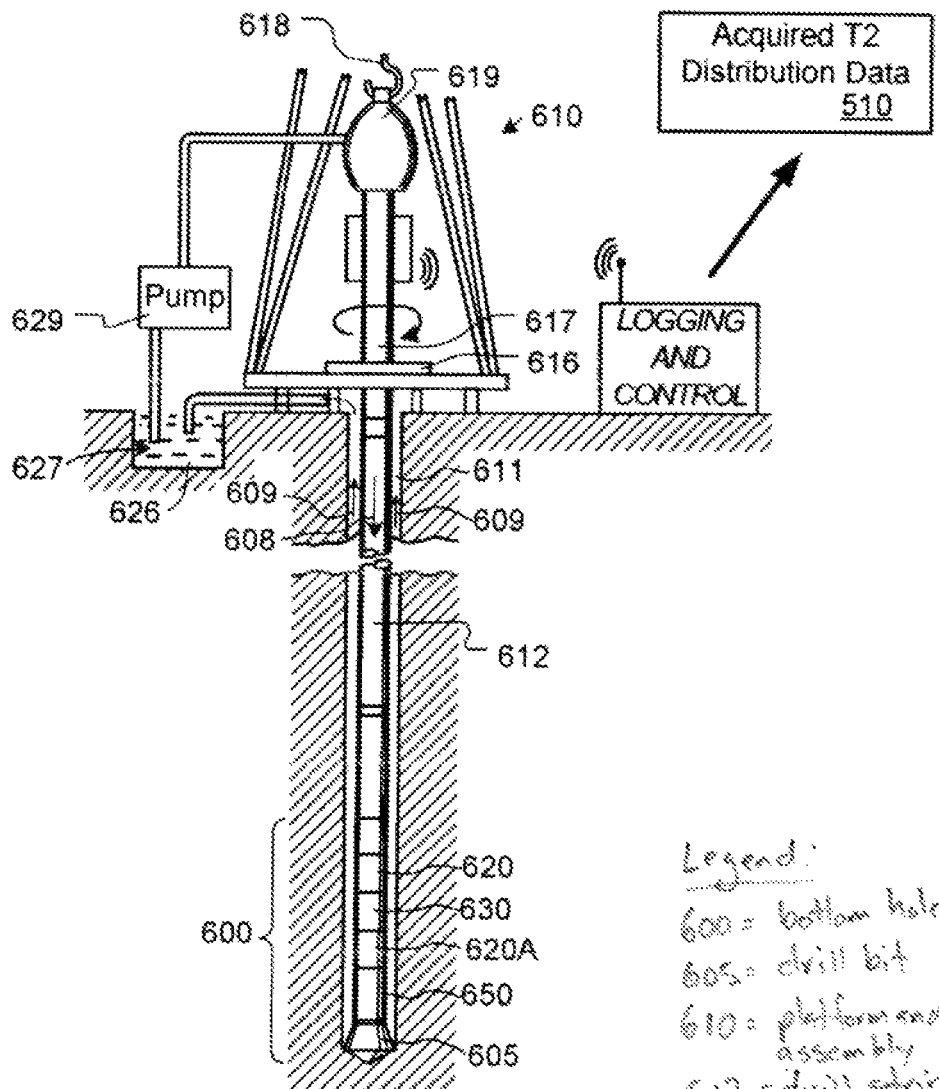
FIG. 6 illustrates a wellsite system in which the subject disclosure can be employed.

FIG. 6 illustrates a wellsite system in which the subject disclosure can be employed. The wellsite can be onshore or offshore. In this system, a borehole 611 is formed in subsurface formations by rotary drilling in a manner that is well known. Embodiments of the subject disclosure can also use directional drilling, as will be described hereinafter.

A drill string 612 is suspended within the borehole 611 and has a bottom hole assembly 600 which includes a drill bit 605 at its lower end. The surface system includes platform and derrick assembly 610 positioned over the borehole 611, the assembly 610 including a rotary table 616, kelly 617, hook 618 and rotary swivel 619. The drill string 612 is rotated by the rotary table 616, energized by means not shown, which engages the kelly 617 at the upper end of the drill string. The drill string 612 is suspended from a hook 618, attached to a traveling block (also not shown), through the kelly 617 and a rotary swivel 619 which permits rotation of the drill string relative to the hook. As is well known, a top drive system could alternatively be used.

In the example of this embodiment, the surface system further includes drilling fluid or mud 626 stored in a pit 627 formed at the well site. A pump 629 delivers the drilling fluid 626 to the interior of the drill string 612 via a port in the swivel 619, causing the drilling fluid to flow downwardly through the drill string 612 as indicated by the directional arrow 608. The drilling fluid exits the drill string 612 via ports in the drill bit 605, and then circulates upwardly through the annulus region between the outside of the drill string and the wall of the borehole, as indicated by the directional arrows 609. In this well known manner, the drilling fluid lubricates the drill bit 605 and carries formation cuttings up to the surface as it is returned to the pit 627 for recirculation.

The bottom hole assembly 600 of the illustrates a logging-while-drilling (LWD) module 620, a measuring-while-drilling (MWD) module 630, a roto-steerable system and motor, and drill bit 605.

The LWD module 620 is housed in a special type of drill collar, as is known in the art, and can contain one or a plurality of known types of logging tools. It will also be understood that more than one LWD and/or MWD module can be employed, e.g., as represented at 620A. (References, throughout, to a module at the position of 620 can alternatively mean a module at the position of 620A as well.) The LWD module includes capabilities for measuring, processing, and storing information, as well as for communicating with the surface equipment. In the present embodiment, the LWD module includes a nuclear magnetic resonance measuring device.

The MWD module 630 is also housed in a special type of drill collar, as is known in the art, and can contain one or more devices for measuring characteristics of the drill string and drill bit. The MWD tool further includes an apparatus (not shown) for generating electrical power to the downhole system. This may include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device and an inclination measuring device.

Figure 7:
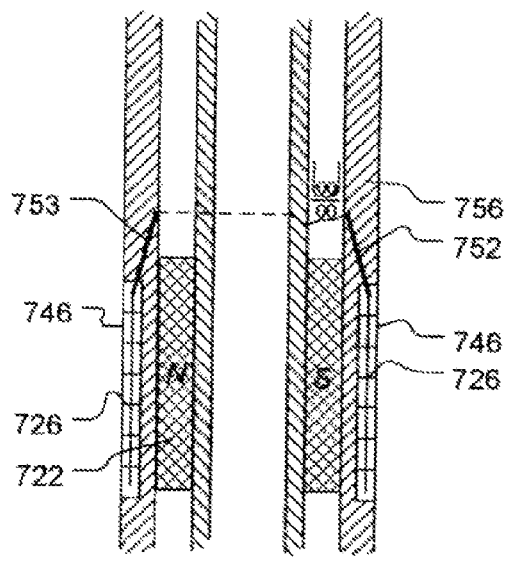
FIG. 7 shows further detail of a device for formation evaluation while drilling using pulsed nuclear magnetic resonance, according to some embodiments.

FIG. 7 shows an embodiment of a type of device described in U.S. Pat. No. 5,629,623 for formation evaluation while drilling using pulsed nuclear magnetic resonance (NMR), incorporated herein by reference, it being understood that other types of NMR/LWD tools can also be utilized as the LWD tool 620 or part of an LWD tool suite 620A. As described in the '623 Patent, an embodiment of one configuration of the device comprises a modified drill collar having an axial groove or slot that is filled with ceramic insulator, and contains RF antenna 726, which is protected by a non-magnetic cover 746, and produces and receives pulsed RF electromagnetic energy. The conductors of the RF antenna are grounded at one end to the drill collar. At the other end, the conductors are coupled to an RF transformer 756 via pressure feed-throughs 752 and 753. The transformer 756 keeps a 180° phase difference between the currents in diametrically opposite RF conductors. A cylindrical magnet 722 produces a static magnetic field in the formations. The RF antenna can also be arranged so that the drill collar itself produces the oscillating RF magnetic field. The oscillating RF magnetic field, which excites nuclei of substances in the formations, is axially symmetric, to facilitate measurements during rotation of the drill string. According to some embodiments, the NMR/LWD tool shown in FIGS. 6 and 7 transmit T2 distribution data 510 to a processing center at the surface such as center 550 shown in FIG. 5 which carries out applying a T2cutoff derived from magnetic susceptibility measurements as described herein. The magnetic susceptibility data can, according to some embodiments be collected using a wireline tool such as tool 526 shown in FIG. 5.

A downhole application of the workflows according to described embodiments would provide a depth curve of T2cutoff, which would yield improved permeability estimations from NMR. By combining a magnetic susceptibility tool and an NMR tool, a dynamic T2cutoff can then be provided, together with the standard NMR log, according to some embodiments. According to some embodiments the improved permeability estimations can be provided automatically and in real time at the wellsite.

Embodiments have so far focused on an automated dynamic determination of T2cutoff based on the described workflow using magnetic susceptibility measurements. According to some alternative embodiments, an automated method for dynamic T2cutoff determination uses other existing measurements to derive rock typing and therefore zoned T2cutoffs. For example, spectroscopy data for tools such as ECS (Elemental Capture Spectroscopy) can be used to derive rock type information (carbonate vs. sandstone, for example) and dynamically change the T2cutoff. Although not as robust as the described methods based on Magnetic susceptibility, such use of spectroscopy data would be relatively straightforward to apply for an automated system.

While the subject disclosure is described through the above embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the subject disclosure should not be viewed as limited except by the scope and spirit of the appended claims.

What is claimed is:

1. A method of determining T2 cutoff in a subterranean rock formation comprising:
   receiving, from a first downhole tool positioned proximate a rock medium in the subterranean rock formation, magnetic susceptibility data representing magnetic susceptibility measurements made of the rock medium;
   utilizing the received magnetic susceptibility data of the rock medium as a proxy in order to calculate over time an estimated value of a T2 cutoff;
   receiving from a second downhole tool, also positioned proximate the rock medium, a T2 distribution of data representing NMR measurements of the rock medium; and
   applying the estimated value of the T2 cutoff to the T2 distribution of data representing NMR measurements of the rock medium, in order to thereby derive one or more of:
   a permeability of the rock medium; and
   a location of a non-moveable fluid in the rock medium;
   wherein one or more of the permeability of the rock medium and the location of the non-moveable fluid in the rock medium is provided as an output to a user.

2. A method according to claim 1 wherein the calculating and applying of the estimated T2 cutoff values are performed automatically.

3. A method according to claim 1 wherein the subterranean rock formation is a hydrocarbon-bearing formation traversed by at least one well bore.

4. A method according to claim 3 wherein the magnetic susceptibility measurements and the NMR measurements are made from within the at least one well bore.

5. A method according to claim 4 wherein the NMR and magnetic susceptibility measurements are made using one or more wireline tools.

6. A method according to claim 4 wherein the NMR measurements are made using an LWD tool during a drilling operation.

7. A method according to claim 4 wherein the magnetic susceptibility data and T2 distribution data, form depth logs along a depth of the at least one well bore, and the calculating over time of the estimated value for T2 cutoff is performed repeatedly over a plurality of depths in order to yield dynamic T2 cutoff data.

8. A method according to claim 1 wherein calculating of the estimated value of the T2 cutoff makes use of a relationship:

$$T_2 \approx \frac{1}{A*\chi + B},$$

where $\chi$ represents magnetic susceptibility and A and B are constants.

9. A method according to claim 4 wherein the calculating and applying of the estimated T2 cutoff values are performed at a location local to the at least one well bore.

10. A method according to claim 4 wherein the calculating and applying of the estimated T2 cutoff values are performed at a location remote from the at least one well bore.

11. A system that evaluates a hydrocarbon-bearing subterranean rock formation comprising:
    a magnetic susceptibility tool configured for making magnetic susceptibility measurements of the hydrocarbon-bearing subterranean rock formation from within a borehole;
    a nuclear magnetic resonance tool configured for making T2 distribution measurements of the hydrocarbon-bearing subterranean rock formation from within a borehole; and
    a processing system configured and programmed in order to:
    form an evaluation of the hydrocarbon-bearing subterranean rock formation by utilizing the magnetic susceptibility measurements of the hydrocarbon-bearing subterranean rock formation in order to calculate over time an estimated value of a T2 cutoff using a relationship:

$$\frac{1}{A*\chi + B},$$

where $\chi$ represents magnetic susceptibility and A and B are constants, and applying the estimated value of the T2 cutoff to the T2 distribution measurements of the hydrocarbon-bearing subterranean rock formation;
wherein the evaluation of the hydrocarbon-bearing subterranean rock formation is provided as an output to a user.

12. A system according to claim 11 wherein the magnetic susceptibility tool is a wireline tool and the nuclear magnetic resonance tool is a wireline tool.

13. A system according to claim 11 wherein the nuclear magnetic resonance tool is an LWD tool.

14. A system according to claim 11 wherein the processing system is further configured and programmed to continuously calculate estimated values for T2 cutoff and apply the estimated values to T2 distribution data over a depth interval, so as to yield a permeability log over the depth interval.

15. A method of generating values of a T2 cutoff and permeability over a depth interval of a wellbore traversing a subterranean rock formation comprising:
    receiving downhole data representing magnetic susceptibility measurements made at a plurality of depths within the depth interval of the rock formation;

utilizing the magnetic susceptibility measurements in order to calculate over time estimated values of a T2 cutoff for each of the plurality of depths within the depth interval using a relationship:

$$T_2 \approx \frac{1}{A*\chi + B},$$

where $\chi$ represents magnetic susceptibility and A and B are constants;

receiving a T2 distribution of data representing NMR measurements made at the plurality of depths within the depth interval; and applying the estimated values of the T2 cutoff to the T2 distribution of data in order to yield permeability data at each of the plurality of depths within the depth interval; wherein at least some of the permeability data is provided as an output to a user.

16. A method according to claim 15 wherein the receiving of data, utilizing and applying are performed automatically.

17. A method according to claim 15 wherein the yielded permeability data has a vertical resolution of at most one meter.

18. A method according to claim 15 wherein the downhole data representing magnetic susceptibility and the T2 distribution of data representing NMR measurements are collected using one or more wireline tools.

19. A method according to claim 15 wherein the method is performed at a wellsite near the wellbore.

20. A method according to claim 15 wherein the method is performed continuously as the measurements are being made.

* * * * *